United States Patent [19]
Bloch et al.

[11] Patent Number: 5,636,626
[45] Date of Patent: Jun. 10, 1997

[54] PROCESS AND DEVICE FOR THE PREPARATION OF A GASEOUS MIXTURE COMPRISED BY A VECTOR GAS AND A VAPORIZED ADDITIVE

[75] Inventors: Nicolas Bloch, Paris; Stéphane Ruton, Viroflay, both of France

[73] Assignee: Taema, Antony Cedex, France

[21] Appl. No.: 560,679

[22] Filed: Nov. 20, 1995

[30] Foreign Application Priority Data

Nov. 23, 1994 [FR] France .................................. 94 14037

[51] Int. Cl.$^6$ .................................................. A61M 15/00
[52] U.S. Cl. ........................ 128/203.12; 128/202.22; 128/203.24; 128/203.25
[58] Field of Search ........................ 128/202.22, 203.12, 128/203.24, 203.25

[56] References Cited

U.S. PATENT DOCUMENTS 3,528,418  9/1970  Grosholz et al. .................. 128/200.13
4,484,576  11/1984  Albarda ........................... 128/202.22

FOREIGN PATENT DOCUMENTS 0 231 513  8/1987  European Pat. Off. .
0 243 259  9/1988  European Pat. Off. .
0 280 846  9/1988  European Pat. Off. .
2 253 353  9/1992  United Kingdom .

*Primary Examiner*—Aaron J. Lewis
*Attorney, Agent, or Firm*—Young & Thompson

[57] ABSTRACT

A sealed receptacle (1) contains the additive in liquid phase. A dip tube (3) permits sending the additive to a heating enclosure (5) in which the liquid vaporizes before being sent to a collector-mixer (11) through a constriction (10). The flow rate of additive is controlled by the pressure prevailing above the liquid in the receptacle (1) thanks to a control valve (20) connected by a pressure regulator (25) to a computer (26). This latter receives predetermined values of concentration of the mixture through an input (27). It is preferably connected to a detector (28) of the temperature of the enclosure and/or to an analyzer (30) of the composition of the mixture. Used particularly in anesthesia apparatus.

9 Claims, 1 Drawing Sheet

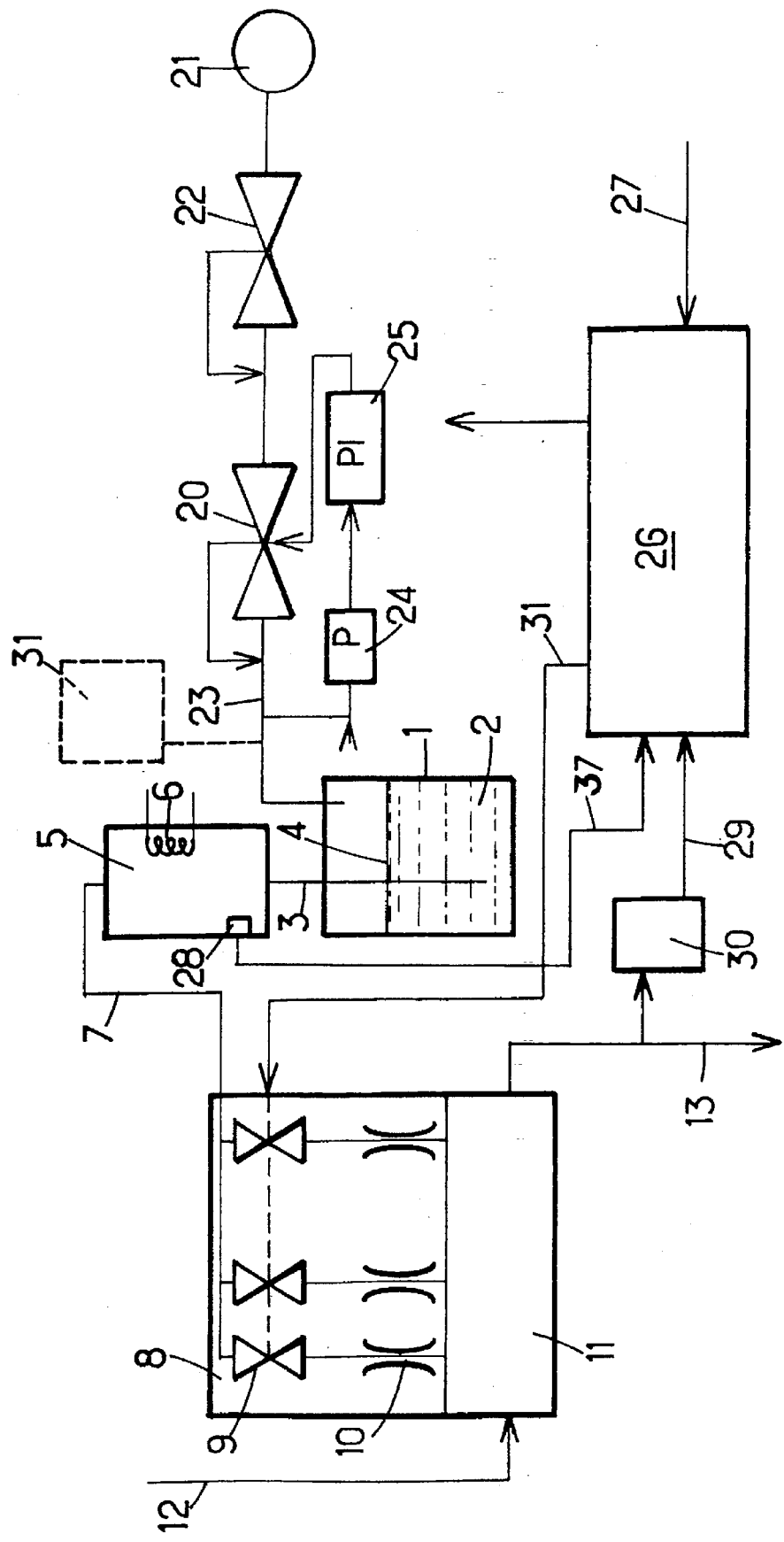

PROCESS AND DEVICE FOR THE PREPARATION OF A GASEOUS MIXTURE COMPRISED BY A VECTOR GAS AND A VAPORIZED ADDITIVE

FIELD OF THE INVENTION

The present invention relates to a process and a device for the preparation of a circulating gaseous mixture containing a defined proportion of an addition element, particularly for the production of anesthetic gaseous mixtures.

BACKGROUND OF THE INVENTION

The document EP-A-0.231.513 describes a device for obtaining gaseous mixtures, particularly anesthetic, comprised by a vector gas in which is injected a measured quantity of an additive. The device comprises a closed chamber, maintained at constant temperature and pressure, this pressure and this temperature being such that the additive is in gaseous phase. An outlet passage connects the enclosure to a conduit into which is sent the vector gas. This passage is provided with measuring means constituted by a valve which is cyclicly opened and/or a valve constituting an adjustable constriction. The enclosure is connected to a closed receptacle containing the additive in liquid phase, such that, each time the additive leaves the enclosure through the outlet passage, an equal mass of liquid additive enters the enclosure to be vaporized therein. To do this, it suffices that the liquid level in the receptacle be lower than the enclosure, that the connection between the receptacle and the enclosure be provided by a tube which dips into the liquid, and that the pressure above the liquid be defined as a function of the pressure which it is desired to maintain in the enclosure.

In the device described in the cited document, the regulation of the additive flow rate through the outlet passage, which is to say finally the additive content of the mixture, is carried out by acting on the frequency of opening of the valve in the outlet passage.

This operative mode has the drawback that it has no intrinsic safety: if the adjustment valve becomes blocked in open position, or closed position, in the course of anesthesia, the consequences can be immediately serious.

It will also be noted that the pressure in the enclosure must always be substantially less than that which corresponds to the boiling of the liquid at the temperature in this enclosure. Thus, if the pressure in the enclosure were to mount beyond this limit value, the dosage means would begin to add the additive in liquid phase and no longer in gaseous phase. There would result a very abrupt increase, and possibly very dangerous, of the additive content of the mixture. Such an accident could take place as a result of stopping the heating means of the enclosure. As the operation is at constant pressure, it would thereby be necessary that the safety means block the measuring means before the liquid additive can reach the latter. In this case, stopping heating would give rise to an abrupt fall in the additive content of the mixture.

The apparatus must therefore be associated with alarm and safety devices which respond very rapidly, which increase its complication and cost.

Another drawback of the device described in the mentioned document results from the fact that the adjustment of the additive flow rate is made by acting on the frequency of opening the measuring valve. For small contents, the frequency could fall to 0.1 Hz, namely one pulse every ten seconds. Such low frequencies can require the presence, downstream, of a mixing means, which is a further complication.

SUMMARY OF THE INVENTION

The present invention has for its object to overcome these drawbacks, and to provide a process for obtaining circulating gaseous mixtures which will be safe, simple and effective, in which a malfunction of the regulation means will have a reduced influence on the content of the mixture, and which supply directly a mixture of constant content.

To this end, according to the invention, the process for providing a gaseous mixture formed by a vector gas and at least one vaporized additive, comprising the steps of vaporizing measured quantities of additive contained in liquid phase in a receptacle from which it is expelled toward a vaporizer by expelling gas under pressure introduced into the receptacle, is characterized in that the additive flow rate of additive introduced into the vector gas is adjusted by acting on the pressure of the expelling gas.

A practical means to regulate the gas pressure are an expander in the case of the gas from a pressurized receptacle, or a regulator in the case of a pump. In one or the other case, the materials are of high reliability. Moreover, if the gas supply is accidentally interrupted, the gases contained in the receptacle and in the heating enclosure constitute a backup volume. As a result, the pressure in the vaporizer varies only slowly in the case of an incident, as does also the additive flow rate. This gives the personnel time to intervene to take the necessary measures. For greater safety, a complementary backup reservoir can be connected to the upper portion of the receptacle.

On the other hand, because the pressure is the controlling parameter, it is easy to connect the control means for the pressure with a detector sensitive to the temperature of the vaporization enclosure, such that, in the case of undesired drop of the temperature of the enclosure, the pressure is lowered, either as a function of said temperature, or according to a previously fixed law, so as always to maintain the pressure in the enclosure at a value lower than the pressure at which the liquid vaporizes at the instantaneous pressure of the enclosure.

Finally, the fact that the additive flow rate is controlled as a function of the pressure permits avoiding a variable frequency valve between the vaporizer and the mixture distribution conduit. One can thus use a simple valve, or a constriction, which, for a fixed given pressure, permits the passage of a flow rate which is substantially constant with time, which permits directly obtaining a mixture of constant additive content.

According to a preferred modification, the flow rate control means of the vaporized additive comprises a set of constrictions of different cross sections, and one or several of these constrictions are placed in action and out of action as a function of the general conditions of execution.

Preferably, one or several constrictions of said set are switched for one or several other constrictions when the control pressure approaches within a predetermined distance of a previously selected limit pressure.

For reasons of safety, it is preferable to provide controls of the composition of the gaseous mixture, and an alarm is triggered when the content of additive departs from previously fixed limits. The controls can be continuous or periodic, with a previously fixed frequency.

According to an optional mode of operation, to obtain greater regularity of the composition of the mixture, the control means for the composition of the gaseous mixture are preferably part of a system of the "closed loop" type, which is to say that the pressure of the gas sent to the receptacle is modified if desired as a function of the result of the controls.

BRIEF DESCRIPTION OF THE DRAWINGS

The invention will now be described in more detailed fashion with the aid of a practical example, shown in the single FIGURE, which is a schematic view of an apparatus according to the invention.

DETAILED DESCRIPTION OF THE INVENTION

The device used by way of example comprises:

A pressurizable receptacle 1 containing a quantity of liquid additive 2, a dip tube 3, which passes through the wall of the receptacle 1, extends below the level 4 of the liquid additive and leads to a heating enclosure 5 of a vaporizer, maintained at a suitable temperature by a heating resistance 6, and an outlet conduit 7, connecting the heating enclosure to a flow rate control assembly 8.

This assembly 8 comprises several passages disposed in parallel, each comprising in series a valve 9 and a fixed constriction 10. By regulating the number of open or closed valves 9 and/or the section of the passage of the constrictions 10, there can be obtained a wide range of flow rates. The constrictions 10 open into a collector-mixer 11, in which carrier gas supplied by a supply conduit 12 enters at one end, whilst the mixture leaves by an opposite end to be distributed by a distribution conduit 13. The means to control the pressure within the interior of the receptacle 1 comprises essentially a control valve 20 disposed downstream of an expander 22, in a line 23 connecting the receptacle 1 to a source of gas under pressure 21. The source of gas under pressure 21 can be of any type, provided that its pressure be within suitable limits, here 2 to $8 \times 10^5$ Pa. In practice, there is preferably chosen the oxygen network of a hospital assembly, which has the advantage of being accessible at a large number of points.

On the end of conduit 23 which opens into the upper portion of the receptacle, is connected a pressure detector 24 which accordingly indicates the pressure prevailing within the receptacle 1. The detector 24 is connected to a pressure regulator 25, which is for example a regulator of the "centronic" type sold by the French company Joucomatic, but which can be no matter what type of regulator having comparable performance.

An electronic computer 26, with a microcomputer and ROM and RAM memories, establishes the value of the control pressure which is transmitted to the regulator 25. The computer 26 receives through an input 27 a predetermined value of the composition of the mixture to be produced. An inlet line 37 connects an input of the computer to a temperature detector 28 installed in the heating enclosure 5 and another input line 29 transmits to the computer 26 signals as to the composition of the exiting mixture, emitted by an analyzer 30 connected to the distribution conduit 13.

There is shown in broken line a buffer reservoir 31 which can be provided to slow the pressure drop in the receptacle 1 in the case of abrupt untimely stopping of the pressure source 21.

A first series of tests has been run with the apparatus which has been described. In these tests, the carrier gas is air and the additive halothane. The temperature in the heating enclosure 5 is 80° C. There are obtained the following results:

| Vector gas flow rate (l/m) | Concentration (% vol) | P liquid (kPa) | Gas flow rate (ml/mn) |
|---|---|---|---|
| 0.5 | 3 | 11.1 | 15 |
| 10 | 0.2 | 17.4 | 20 |
| 15 | 0.4 | 80.0 | 60 |
| 20 | 1 | 74.4 | 200 |

It will be seen that the process and apparatus according to the invention permit covering a very wide range of flow rates and of concentration.

We claim:

1. Process for preparing a gaseous mixture comprised of a vector gas and at least one vaporized additive comprising:
   providing a receptacle containing at least a liquid additive;
   providing control valve means disposed in a conduit connecting a source of expulsion gas under pressure and the receptacle;
   supplying expulsion gas under pressure above the level of liquid additive into the receptacle, thereby modifying the pressure in said receptacle;
   providing a delivery circuit including means for distributing additive to a vector gas circuit and comprising, in series,
      a dip tube extending below the level of liquid additive into the receptacle,
      a vaporizer fluidly connected to said dip tube for vaporizing liquid additive fed to said vaporizer via said dip tube, and
      flow rate control means for controlling the flow rate of vaporized additive;
   expelling toward said vaporizer via said tube measured quantities of liquid additive;
   vaporizing said expelled measured quantities of liquid additive;
   mixing obtained vaporized measured quantities of liquid additive with vector gas; and
   actuating said control valve means as a function of a signal corresponding to the pressure in said receptacle.

2. Process according to claim 1, further comprising controlling the composition of the gaseous mixture, and triggering an alarm when the content of additive departs from previously fixed limits.

3. Process according to claim 1, wherein controls of the composition of the gaseous mixture are provided, and modifying the pressure of the expulsion gas supplied to the receptacle responsive to said controls.

4. Process according to claim 1, further comprising adjusting the pressure of the expulsion gas as a function of the pressure in the receptacle.

5. Process according to claim 1, further comprising adjusting the pressure of the expulsion gas as a function of the temperature in the vaporizer.

6. Process according to claim 1, further comprising adjusting the pressure of the expulsion gas as a function of the content of a component of the gaseous mixture.

7. Process according to claim 1, wherein the expulsion gas is oxygen.

8. Device for preparing a gaseous mixture comprised of a vector gas and at least one vaporized additive comprising:
   a receptacle containing at least a liquid additive;
   means for supplying an expulsion gas under pressure above the level of liquid additive into the receptacle, thereby modifying the pressure in said receptacle;

a delivery circuit including means for distributing additive to a vector gas circuit and comprising, in series,
   a dip tube extending below the level of liquid additive into the receptacle,
   a vaporizer fluidly connected to said dip tube for vaporizing liquid additive fed to said vaporizer via said dip tube, and
   flow rate control means for controlling the flow rate of vaporized additive;
said means for supplying said expulsion gas comprising control valve means disposed in a conduit connecting a source expulsion gas under pressure and the receptacle containing liquid additive, and actuated as a function of a signal corresponding to the pressure in said receptacle.

9. Device according to claim 8, which further comprises at least one detector of a parameter in the delivery circuit coupled with a computer supplying control signals by means of a control valve as a function of the detected parameter.

* * * * *